United States Patent [19]

Huang et al.

[11] Patent Number: 4,585,758
[45] Date of Patent: Apr. 29, 1986

[54] ANGIOTENSIN-CONVERTING ENZYME INHIBITORS

[75] Inventors: Fu-chih Huang, Boonton, N.J.; John T. Suh, Greenwich, Conn.; Jerry W. Skiles, Tuckahoe, N.Y.

[73] Assignee: USV Pharmaceutical Corp., Tarrytown, N.Y.

[21] Appl. No.: 690,386

[22] Filed: Jan. 10, 1985

Related U.S. Application Data

[63] Continuation of Ser. No. 496,756, May 20, 1983, abandoned.

[51] Int. Cl.$^4$ .................. A61K 31/47; A61K 37/64; C07K 5/06; C07D 217/06
[52] U.S. Cl. ................ 514/19; 260/112.5 R; 514/307; 546/147
[58] Field of Search ............... 260/112.5 R; 546/147; 514/19, 307

[56] References Cited

U.S. PATENT DOCUMENTS 4,374,829 2/1983 Harris et al. .............. 260/112.5 R
4,499,079 2/1985 Gordon et al. ..................... 514/2

FOREIGN PATENT DOCUMENTS 0050800 5/1982 European Pat. Off. ..... 260/112.5 R

Primary Examiner—Delbert R. Phillips

[57] ABSTRACT

Compounds of the formula

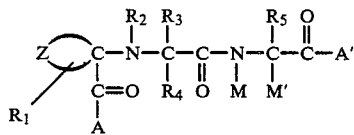

and their pharmaceutically acceptable salts, wherein the substituents are as defined herein, having antihypertensive activity.

18 Claims, No Drawings

ANGIOTENSIN-CONVERTING ENZYME INHIBITORS

This application is a continuation of our previous application Ser. No. 496,756 filed May 20, 1983, abandoned.

BACKGROUND OF THE INVENTION

This application relates to compounds, their pharmaceutically acceptable salts, and pharmaceutical preparations made therefrom, having biological activity as inhibitors of the enzymatic conversion of angiotensin I to angiotensin II. As such, the products comprising the present invention have utility in the treatment of hypertension in subjects suffering therefrom.

SUMMARY OF THE INVENTION

Broadly stated, the present invention comprises compounds of the formula

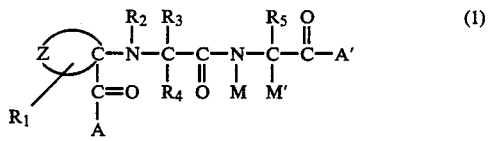

and their pharmaceutically-acceptable salts, wherein

A and A' are independently hydroxy, lower alkoxy, lower alkenoxy, mono- or diloweralkylamino lower alkoxy, acylamino lower alkoxy, acyloxy lower alkoxy, aryloxy, aryl-loweralkyloxy, amino, loweralkylamino, diloweralkylamino, aryl-loweralkylamino, hydroxyamino, or substituted aryloxy, or substituted aryl-loweralkoxy wherein the substituent is methyl, halo or methoxy;

$R_1$ is hydrogen, lower alkyl, aryl, aralkyl, fused cycloalkyl-aryl, or fused aryl-cycloalkyl;

$R_2$, $R_3$, $R_4$ and $R_5$ are independently hydrogen, lower alkyl, lower alkenyl, lower alkynyl, aryl, fused cycloalkyl-aryl, fused aryl-cycloalkyl, aralkyl, cycloalkyl, or heterocyclic, or wherein $R_2$ and $R_3$ taken together with the nitrogen and carbon atoms to which they are respectively attached form an N-heterocyclic ring containing from 3 to 5 carbon atoms or 2 to 4 carbon atoms and a sulfur atom;

M is hydrogen, alkyl, alkenyl, alkynyl, cycloalkyl, acyl, cycloalkyl-alkyl, polycycloalkyl, polycycloalkyl-alkyl, aryl, aralkyl, heteroaryl, heteroaryl-alkyl, heterocycloalkyl, heterocycloalkyl-alkyl, fused polycyclic aryl, fused cycloalkyl-aryl, fused aryl-cycloalkyl, fused aryl-cycloalkyl-alkyl, fused heteroaryl-cycloalkyl, fused heteroaryl-cycloalkyl-alkyl, alkoxyalkyl, alkylthioalkyl, alkyl-amino-alkyl, or dialkylaminoalkyl, M' is hydrogen, loweralkyl, cycloalkyl, phenyl, phenyl lower alkyl, hydroxy phenyl lower alkyl, hydroxy lower alkyl, amino lower alkyl, guanidino lower alkyl, imidazolyl lower alkyl, indolyl lower alkyl, mercapto lower alkyl or lower alkyl thio lower alkyl, or M and M' may be connected together to form a saturated or unsaturated bridge of from 2 to 5 carbon atoms; from 2 to 4 carbon atoms and one oxygen or sulfur atom; fused aralkylene; fused cycloalkyl-alkylene; or a bridge as above, or fused aralkylene, substituted with hydroxy, lower alkoxy, or lower alkyl; and Z contains 2, 3, 4 or 5 carbon atoms, and optionally an O, N, or S atom, and is saturated or contains at most one double bond between adjacent carbon atoms;

wherein the alkyl, alkenyl, and alkynyl groups may carry substituents selected from the group consisting of hydroxy, alkoxy, amino, mono- or dialkylamino, thio, and alkylmercapto; the cycloalkyl groups may carry substituents selected from the group consisting of alkyl, hydroxy, alkylamino, nitro and trifluoromethyl; and the aryl, fused ring, and heterocyclic groups may carry substituents selected from the group consisting of carboxylic acid, lower alkoxycarbonyl, alkyl, hydroxy, alkoxy, hydroxyalkyl, halo, haloalkyl, mercapto, alkylthio, mercaptoalkyl, amino, alkylamino, aminoalkyl, nitro, and methylenedioxy, and trifluoromethyl.

DESCRIPTION OF THE PREFERRED EMBODIMENTS

Preferred compounds of the present invention are those of the general formula given above in which $R_1$, $R_2$, $R_3$, $R_4$ and $R_5$ are each hydrogen or lower alkyl; M is phenethyl, 5-indanyl, 2-indanyl, or tolyl, or is taken together with M' and the N and C atoms to which M and M' are respectively attached, to form an alkylene bridge 2 to 4 carbon atoms in length, or a dihydroindole or tetrahydroisoquinoline ring structure; Z forms a cyclopropyl, cyclobutyl, cyclopentyl or cyclohexyl ring; and A and A' are each hydroxy or lower alkoxy.

The alkyl groups per se and the alkyl moieties in alkoxy, aralkyl, cycloalkyl, aminoalkyl, acyl, and the like, may be straight-chained or branched and preferably contain from 1 to 20 carbon atoms. Such groups include methyl, ethyl, propyl, isopropyl, butyl, isobutyl, tertiary-butyl, amyl, iso-amyl, hexyl, octyl, dodecyl, and the like. Preferably the alkyl groups are lower alkyl containing from 1 to 6 carbon atoms.

The alkenyl and alkynyl groups and moieties can also be straight or branched-chained groups containing from 2 to 20, and preferably 2 to 6, carbon atoms. Such groups include vinyl, ethynyl, propenyl, alkyl, isopropenyl, and the like.

The acyl group includes groups such as alkanoyl, aroyl, sulfonyl, carbamoyl, and the like.

These alkyl, alkenyl, and alkynyl groups can carry substituents such as hydroxy, alkoxy, amino, alkylamino, dialkylamino, mercapto, alkylmercapto, halo, and the like.

The cycloalkyl, polycycloalkyl, aryl, heteroaryl, arylalkyl, fused aryl-cycloalkyl groups and the like contain from 3 to 16 carbon atoms and may carry substituents such as lower alkyl, alkenyl, alkynyl, hydroxyl, mercapto, amino, keto-oxygen, alkoxy, alkylmercapto, alkylamino, dialkylamino, halo, trifluoromethyl and the like. The groups include such radicals as cyclopropyl, cyclobutyl, cyclopentyl, cyclohexyl, cycloheptyl, adamantyl, norbornyl, phenyl, tolyl, benzyl, phenethyl, dimethoxyphenyl, hydroxybenzyl, indanyl, naphthyl, tetrahydronaphthyl, decanhydronaphthyl, pyridyl, quinolyl, pyrrolidyl, pyrrolyl, morpholinyl, furyl, furfuryl, tetrahydrofurfuryl, benzimidazolyl, thienyl, imidazolyl, and the like.

The halo groups include fluoro, chloro, bromo and iodo.

Compounds in accordance with the present invention are readily prepared employing known starting materials and procedures. It will be understood by those skilled in the art that compounds within the present invention can have one or more asymmetric carbons each of which is in the (R) or (S) configuration. All combinations of configurations are within the scope of the invention; the preferred compounds are those in the (S), (S,S), or (S,S,S) form.

The present new compunds can be prepared by reacting a cycloalkyl or cycloalkenyl compound of the formula (2)

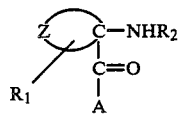
(2)

with a compound of the formula

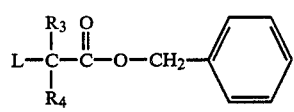
(3)

in which the symbols $R_1$, $R_2$, $R_3$, $R_4$, A and Z are as defined hereinabove, and L is a leaving group such as iodide, chloride, or bromide. The product of the reaction of compounds (2) and (3) has the formula

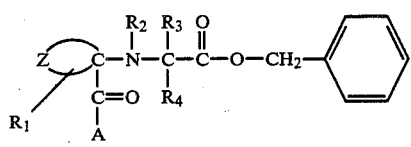
(4)

This compound (4) is hydrogenated, e.g., over palladium and charcoal to form compound (5):

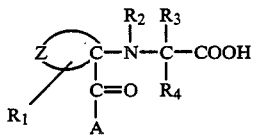
(5)

Compound (5) is then reacted with an appropriate amino compound (6) of the formula

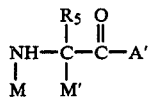
(6)

wherein M, M', and $R_5$ have the definitions given hereinabove, and A' is preferably lower alkoxy or benzyloxy. The reaction is carried out by conventional peptide coupling techniques, in the presence of a coupling agent such as DCC (N,N'-dicyclohexylcarbodiimide), to form the amide having the general structure (1) given above. The compound (6) can comprise a cyclic compound (7)

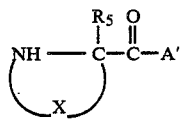
(7)

wherein X symbolizes the heterocyclic or fused cycloalkyl-aryl ring formed by joining M and M' as described previously. A' is subsequently converted, if desired, to the acid, by means well-known in this art.

Each of the above reactions proceeds in a straightforward manner in a suitable solvent at temperatures ranging from 0° to 180° C.

The products are obtained typically as a mixture of diasteroisomers which can be separated by standard methods of fractional crystallizaion or chromatography.

The compounds of this invention form acid salts with various inorganic and organic acids which are also within the scope of the invention. The pharmaceutically acceptable acid addition salts of the compounds of the present invention may be prepared by conventional reactions by reacting the free amino acid or amino ester with an appropriate acid providing the desired anion, either in a solvent or medium in which the salt is insoluble, or in water and removing the water by freeze drying. The salts of strong acids are preferred. As exemplary, but not limiting, of pharmaceutically acceptable acid salts are the salts of hydrochloric, hydrobromic, sulfuric, nitric, acetic, fumaric, malic, maleic and citric acids.

The action of the enzyme renin or angiotensinogen, a pseudoglobulin in blood plasma, produces the decapeptide angiotensin I. Angiotensin I is converted by angiotensin converting enzyme (ACE) to the octapeptide angiotensin II. The latter is an active pressor substance which has been implicated as the causative agent in various forms of hypertension in various mammalian species, e.g., rats and dogs. The compounds of this invention intervene in the renin-to-angiotension I-to-angiotensin II sequence by inhibiting angiotensin I converting enzyme and reducing or eliminating the formation of the pressor substance angiotensin II and therefore are useful in reducing or relieving hypertension. Thus by the administration of a composition containing one or a combination of compounds of formula (1) or pharmaceutically acceptable salts thereof, hypertension in the species of mammal suffering therefrom is alleviated. A single dose, or preferably two to four divided daily doses, provided on a basis of about 0.1 to 100 mg per kilo-gram per day, preferably about 1 to 50 mg per kilogram per day, is appropriate to reduce blood pressure. The substance is preferably administered orally, but a parenteral route such as subcutaneously, intramucsularly, intravenously or intraperitonealy can also be employed.

The compounds of the invention can be utilized to achieve the reduction of blood pressure by formulating one or more of them in compositions such as tablets, capsules or elixirs for oral administration or in sterile solutions or suspensions for parenteral administration. About 10 to 500 mg of a compound or mixture of compounds of formula (1) or physiologically acceptable salt thereof is compounded with a physiologically acceptable vehicle, carrier, excipient, binder, preservative, stabilizer, flavor, etc., in a unit dosage form as called for by accepted pharmaceutical practice. The amount of active substance in these compositions or preparations is such that a suitable dosage in the range indicated is obtained.

Illustrative of the adjuvants which may be incorporated in tablets, capsules and the like are the following: a binder such as gum tragacanth, acacia, corn starch or gelatin; an excipient such as dicalcium phosphate; a disintegrating agent such as corn starch, potato starch, alginic acid and the like; a lubricant such as magnesium stearate; a sweetening agent such as sucrose, lactose or saccharin; a flavoring agent such as peppermint, oil of wintergreen or cherry. When the dosage unit form is a capsule, it may contain in addition to materials of the above type a liquid carrier such as a fatty oil. Various other materials may be present as coatings or to otherwise modify the physical form of the dosage unit. For instance, tablets may be coated with shellac, sugar or both. A syrup or elixir may contain the active compound, sucrose as a sweetening agent, methyl and propyl parabens as preservatives, a dye and a flavoring such as cherry or orange flavor.

Sterile compositions for injection can be formulated according to conventional pharmaceutical practice by dissolving or suspending the active substance in a vehicle such as water for injection, a naturally occurring vegetable oil like sesame oil, coconut oil, peanut oil, cottonseed oil, etc., or a synthetic fatty vehicle like ethyl oleate, and the like. Buffers, preservatives, antioxidants and the like can be incorporated as required.

Specific embodiments of the invention are illustrated in the following Examples.

EXAMPLE I

N-(1-carbethoxy-1-cyclopentyl)-alanyl-proline t-butyl ester

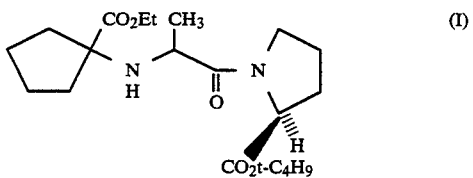

A mixture of ethyl 1-amino-1-cyclopentanoate (10 g), benzyl 2-iodopropionate (20 g), and triethyl amine (6.43 g) in 70 ml of dimethyl formamide was stirred overnight at room temperature and heated at 60° for 1 hour. The solvent was removed under vacuum. The residue was acidified to pH 2 and extracted with ether. The aqueous solution was neutralized to pH 10 and then extracted with ethyl acetate. The combined ethyl acetate extracts were dried and evaporated to dryness. Purification by dry column chromatography gave 9 g of the intermediate product (I-A), ethyl 1-N-(benzyl 2-propionate)-1-amino-1-cyclopentane carboxylate:

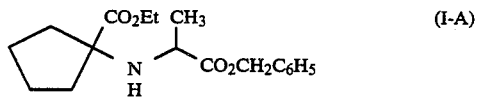

Ten grams of the product (I-A) was hydrogenated with 1.2 g of 5% Pd/C in 150 ml of ethanol at 40 psi for 2.5 hr. After filtration the solvent was evaporated to give 5.5 g of intermediate product (I-B), ethyl 1-N-(2-propionic acid)-1-amino-1-cyclopentane carboxylate:

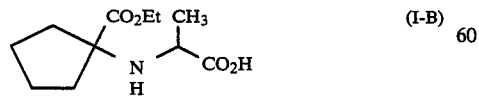

The product (I-B) (3.3 g) in 50 ml of $CH_2Cl_2$ was treated with carbonyl di-imidazole (2.34 g) at room temperature. The reaction mixture was stirred for 30 minutes and then L-proline t-butyl ester (2.5 g) in 10 ml of $CH_2Cl_2$ was added dropwise. After stirring overnight at room temperature, the organic solution was washed well with water, dried and evaporated to give 4.5 g of crude product. Purification by dry column chromatography gave 2.2 g of oily product.

EXAMPLE II

N-(1-carboxy-1-cyclopentyl)-alanyl-proline

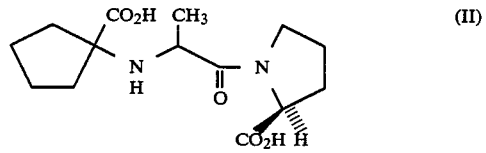

The peptide I from example I (2.2 g) in 50 ml of ether was treated with dry HCl gas for 2 hours at 0° C. The solvent was evaporated and the residue was treated with ethanolic KOH (10 ml, 1N) in 15 ml of dioxane. After evaporation of solvent, the residue was purified on Dowex 50×2−100 (80 ml volume). The peptide was eluted with 3% pyridine. The combined ninhydrin positive fraction was lyophilized to give a white solid product, mp 142°-5°.

EXAMPLE III

N-(1-carbethoxy-1-cyclohexyl)-alanyl-proline t-butyl ester

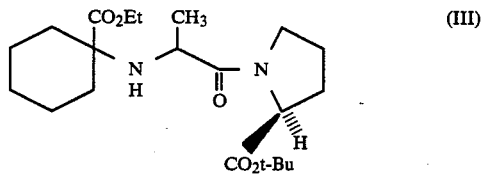

A mixture of ethyl 1-amino-1-cyclohexylcarboxylate (10 g), benzyl 2-iodopropionate (18.5 g), and triethyl amine (6.46 g) in 50 ml of DMF was stirred at 50° C. overnight. DMF was removed under reduced pressure. The residue was dissolved in 1N HCl solution, then washed with ether. The aqueous layer was basified with NaOH to pH 10 and was then extracted with methylene chloride. The combined methylene chloride extracts were dried with magnesium sulfate and concentrated. Purification with dry column chromatography gave 8 g of the intermediate product (III-A), ethyl 1-N-(benzyl-2-propionate)-1-amino-1-cyclohexane carboxylate:

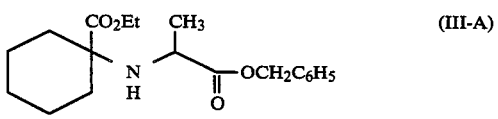

A solution of 4.6 g of compound (III-A) and 1 g of 10% Pd/C in 100 ml of ethanol was hydrogenated at 50 psi for 5 hours. After filtration and evaporation of solvent, 3 g of product (III-B) was obtained, ethyl 1-N-(2-propionic acid)-1-amino-1-cyclohexane carboxylate:

![Structure III-B: cyclohexyl with CO2Et, NH, connected to CH(CH3)CO2H]

To a solution of 2.4 g of a compound (III-B) in 50 ml of dry tetrahydrofuran was added 1.62 g of carbonyldiimidazole. The solution was stirred at room temperature for 40 minutes. L-proline t-butyl ester (1.71 g) was then added and stirring was continued overnight. After evaporation of solvent, the residue was extracted with methylene chloride. The combined organic extracts were dried with magnesium sulfate and concentrated. Purification by dry column chromatography gave 1.8 g of the desired product (III).

EXAMPLE IV

N-(1-carbethoxy-1-cyclohexyl)-alanyl-proline

![Structure IV]

An etheral solution of compound (III) (1.8 g) in 100 ml of ether was treated with dry HCl gas at 0° C. for two hours. Solvent was evaporated. Repeated reprecipitation with methylene chloride and ether gave 1.5 g of hygroscopic product (IV).

EXAMPLE V

N-(1-carboxy-1-cyclohexyl)-alanyl proline

![Structure V]

Compound (IV) from Example IV (0.5 g) in 10 ml of 1 NaOH solution was stirred at room temperature for three days. The reaction mixture was neutralized to pH 7 and lyophilized. Purification through Dowex 50×2−100 resin to remove salts and neutral products gave 0.2 g of product (V).

EXAMPLE VI

N-(1-carbethoxy-1-cyclohexyl)-alanyl-(1,2,3,4-tetrahydro-3-carbomethoxy)isoquinoline ![Structure VI]

To a solution of 1.5 g of compound (III-B) from Example III in 20 ml of methylene chloride was added 10 g of carbonyldiimidazole. The solution was stirred at room temperature for 40 minutes, and then 1.41 g of methyl tetrahydroisoquinoline-3-carboxylate was added. The reaction was continued overnight. The organic solution was washed with water, then with sodium bicarbonate solution, dried with magnesium sulfate, and concentrated. Purification by dry column chromatography gave 1.4 g of product (VI).

EXAMPLE VII

N-(1-carboxy-1-cyclohexyl)-alanyl-(1,2,3,4-tetrahydro-3-carboxyl)isoquinoline

![Structure VII]

Compound (VI) from Example VI (1.4 g) in 10 ml of 1N NaOH solution was stirred at room temperature for 3 days. The reaction mixture was neutralized to pH 7 and then lyophilized. Purification through Dowex 50×2−100 resin (100 ml) to remove salts and neutral products gave 0.6 g of product (VII).

EXAMPLES VIII-X

In a manner wholly analogous to that employed above, the following compounds are also prepared:

VIII: N-(1-carbethoxy-1-cyclopropyl)-alanyl proline t-butyl ester

IX: N-(1-carbethoxy-1-cyclopropyl)-alanyl proline hydrochloride

X: N-(1-carbethoxy-1-cyclopentyl)-lysinyl proline.

We claim:

1. Compounds of the formula

![Claim formula]

and their pharmaceutically-acceptable salts, wherein $R_4$ is lower alkyl or amino-lower alkyl, A and A' are independently hydroxy, lower alkoxy, or benzyloxy, M and M' are connected together to form an alkylene bridge of from 2 to 4 carbon atoms or together with the N and C to which they are connected form a 1,2,3,4-tetrahydro-isoquinoline ring, and Z is —$(CH_2)_2$—, —$(CH_2)_3$—, —$(CH_2)_4$— or —$(CH_2)_5$—.

2. The compounds and salts according to claim 1 wherein M and M' form a 1,2,3,4-tetrahydro-isoquinoline ring.

3. The compound according to claim 2 which is N-(1-carboxy-1-cyclohexyl)-alanyl-(1,2,3,4-tetrahydro-3-carboxy)-isoquinoline, and pharmaceutically acceptable salts thereof.

4. The compound according to claim 2 which is N-(1-carbethoxy-1-cyclohexyl)-alanyl-(1,2,3,4-tetrahydro-3-carboxy)-isoquinoline, and pharmaceutically acceptable salts thereof.

5. The compound according to claim 2 which is N-(1-carbethoxy-1-cyclohexyl)-alanyl-(1,2,3,4-tetrahydro-3-carbomethoxy)-isoquinoline, and pharmaceutically acceptable salts thereof.

6. The compounds and salts according to claim 1 wherein M and M' are connected together to form an alkylene bridge containing 3 carbon atoms.

7. The compound according to claim 6 which is N-(1-carboxy-1-cyclopentyl)-alanyl-L-proline, and pharmaceutically acceptable salts thereof.

8. The compound according to claim 6 which is N-(1-carbethoxy-1-cyclopentyl)-alanyl-L-proline, and pharmaceutically acceptable salts thereof.

9. The compound according to claim 6 which is N-(1-carbethoxy-1-cyclopentyl)-alanyl-L-proline-t-butyl ester, and pharmaceutically acceptable salts thereof.

10. The compound according to claim 6 which is N-(1-carbethoxy-1-cyclohexyl)-alanyl-L-proline, and pharmaceutically acceptable salts thereof.

11. The compound according to claim 6 which is N-(1-carbethoxy-1-cyclohexyl)-alanyl-L-proline-t-butyl ester, and pharmaceutically acceptable salts thereof.

12. The compound according to claim 6 which is N-(1-carboxyl-1-cyclohexyl)-alanyl-L-proline, and pharmaceutically acceptable salts thereof.

13. The compound according to claim 6 which is N-(1-carbethoxy-1-cyclopropyl)-alanyl proline t-butyl ester, and pharmaceutically acceptable salts thereof.

14. The compound according to claim 6 which is N-(1-carbethoxy-1-cyclopropyl)-alanyl proline, and pharmaceutically acceptable salts thereof.

15. The compound according to claim 6 which is N-(1-carbethoxy-1-cyclopentyl)-lysinyl proline, and pharmaceutically acceptable salts thereof.

16. The compounds and salts of claim 9 wherein there is at least one asymmetrical carbon atom, and the substituents on each asymmetrical carbon atom are in the (S) configuration.

17. An antihypertensive therapeutic composition comprising, in combination with at least one nontoxic pharmaceutically-acceptable extender, an angiotensin converting enzyme inhibitory amount of at least one compound or salt of claim 1.

18. A method of treating angiotensin related hypertension which comprises administering to a host suffering therefrom a therapeutically-effective amount of at least one compound or salt of claim 1.

* * * * *